United States Patent [19]
Fox

[11] Patent Number: 5,716,000
[45] Date of Patent: Feb. 10, 1998

[54] EMANATOR FOR VOLATILE LIQUIDS

[75] Inventor: Rodney Thomas Fox, Cottingham, Great Britain

[73] Assignee: Reckitt & Colman Products Limited, Hull, England

[21] Appl. No.: 406,922

[22] PCT Filed: Aug. 17, 1993

[86] PCT No.: PCT/GB93/01740

§ 371 Date: Apr. 13, 1995

§ 102(e) Date: Apr. 13, 1995

[87] PCT Pub. No.: WO94/06480

PCT Pub. Date: Mar. 31, 1994

[30] Foreign Application Priority Data

Sep. 22, 1992 [GB] United Kingdom ............ 9219999

[51] Int. Cl.⁶ .................................................. A24F 25/00
[52] U.S. Cl. ...................................... 239/34; 428/449
[58] Field of Search .......................... 239/34, 35, 44; 428/447, 448, 449, 452

[56] References Cited

U.S. PATENT DOCUMENTS

| 4,445,641 | 5/1984 | Baker | 239/6 |
|---|---|---|---|
| 4,634,614 | 1/1987 | Holzner | 239/55 |
| 4,898,328 | 2/1990 | Fox | 239/6 |

FOREIGN PATENT DOCUMENTS

| AO 075 540 | 3/1983 | European Pat. Off. . |
| A0 215 480 | 3/1987 | European Pat. Off. . |
| A 0 260 896 | 3/1988 | United Kingdom . |
| WO81/00051 | 1/1981 | WIPO . |
| WO84/02654 | 7/1984 | WIPO . |
| WO88/01503 | 3/1988 | WIPO . |

*Primary Examiner*—Robert J. Oberleitner
*Assistant Examiner*—C. T. Bartz
*Attorney, Agent, or Firm*—Fish & Richardson P.C.

[57] ABSTRACT

A device for dispensing a volatile liquid as a vapour which comprises a reservoir of the volatile liquid and which includes a porous element which permits the passage of vapour therethrough but does not permit the passage of the liquid therethrough, characterized in that the porous element comprises a laminate of paper/polymer/paper, the polymer being selected from an ethylene/vinyl acetate copolymer and/or an ionomer resin, and in that the volatile liquid comprises one or more fragrance components having a dipole moment in the range of from 0 to 3 Debyes and a hydrogen bonding parameter of from 0 to 22 Gordys.

9 Claims, 9 Drawing Sheets

EMANATOR FOR VOLATILE LIQUIDS

FIELD OF THE INVENTION

The present invention relates to an emanator for volatile liquids and, in particular, to a device for dispensing liquid substances, such as fragrances, as vapours from containers thereof.

BACKGROUND OF THE INVENTION

Means for the slow release of vapour from containers of liquids are well known, particularly in the field of air fresheners and insecticides.

Commonly, a suitable substrate such as cellulose wadding impregnated with, for example, a perfume oil and/or a volatile liquid insecticidal composition is supported on a frame which is at least partly coverable by a structure limiting the exposure of the wad to the atmosphere, so to give control over the extent of treatment of the environment by a user. Such arrangements sometimes give little or no control over the rate of use by the user and certainly there is no indication of when the pad is exhausted, that is when it has become ineffective, although still possessing an odour or discoloration due to the perfume or insecticide.

Alternatively, wicks immersed at one end in a liquid contained in a clear bottle are adjustably exposed to the atmosphere at the other end from where the vapour emanates in a controllable fashion with an adjustable wick. The rate of usage is high and hence diluted liquids are necessary, which leads to relatively large bottles. In addition such arrangements are generally closable by a cap and there is a danger of spillage if the bottle is left unattended without a cap.

More recently a rupturable sachet of perfume has appeared on the market which sachet is contained in an outer sachet, both sachets being at least translucent. Such a sachet combination is mounted on a suitable framework, optionally assisting rupture of the inner sachet. These devices depend for shelf life upon the impermeability of the rupturable inner sachet membrane. Extreme care needs to be exercised in formulating a composition so that leakage during storage does not occur and fractionation of liquid through the outer membrance does not occur during use. There is a clear end-of-life indicator when the liquid is exhausted.

Coated paper has also been used in dispensers for volatile materials. Thus, FR-A-2157732 discloses an insecticide dispenser comprising an outer film which may be applied to a laminate of one or more paper layers, or may be sprayed onto a block of the other components. The preferred material for the outer film is a high density polyethylene.

JP-A-1-131663 discloses an aromatic article comprising an aromatic material packaged by processed paper obtained by laminating a viscose-processed paper onto the outside of a synthetic resin film. The viscose processing renders the film impermeable to liquids but permeable to gases.

It has also been proposed to evaporate volatile treatment liquid through a solid web of silicone material acting as a liquid phase barrier. Whilst several advantages accrue from the use of such silicone barriers, the material is expensive and consequently inflates the cost of devices incorporating relatively great thicknesses of solid silicone.

EP-A-0260896 discloses a device for dispensing a volatile liquid as a vapour, the device including a porous element provided with at least one substantially elastomeric crosslinked organopolysiloxane material produced from a prepolymer or oligomer of viscosity up to 1,000,000 mm$^2$ sec$^{-1}$ at 25° C. which serves to close the pores of the support to passage of liquid and to permit the passage of vapour.

We have found that the organopolysiloxane material used with the porous element limits the types of fragrances which can be used with this device and, in practice, a clay coating has to be provided on a paper substrate, prior to application of the organopolysiloxane coating, so as to give a flat surface allowing a thin coating of the organosiloxane to be used. The clay coating is generally considered to inhibit fragrance release.

SUMMARY OF THE INVENTION

We have now developed a device which will effect the slow release of vapour from liquids contained in normally leak proof containers at substantially linear rates which does not involve the use of an organopolysiloxane and thus enables the device to be used with a wider range of fragrances than the known device.

DETAILED DISCLOSURE

Accordingly, the present invention provides a device for dispensing a volatile liquid as a vapour which comprises a reservoir of the volatile liquid and which includes a porous element which permits the passage of vapour therethrough but does not permit the passage of the liquid therethrough, wherein the porous element comprises a laminate of paper/polymer/paper, the polymer being selected from a copolymer of ethylene and vinyl acetate, hereinafter referred to as "ethylene/vinyl acetate copolymer" and/or an ionomer resin, and the volatile liquid comprises one or more fragrance components having a dipole moment in the range of from 0 to 3 Debyes and a hydrogen bonding parameter of from 0 to 22 Gordys.

With reference to hydrogen bonding, the method of W. Gordy provides a quantitative picture of relative hydrogen bonding. The hydrogen bonding parameter, γ, expressed in Gordys is calculated as:

$$\gamma = \frac{\bar{v}_0 - \bar{v}_1}{10}$$

where $\bar{v}_0$ is the wave number of an infrared spectrum peak of a 1M solution of deuterated methanol in benzene expressed in cm$^{-1}$, i.e. 2681, and $\bar{v}_1$ is the corresponding wave number when benzene is replaced by methanol. The unit of the Gordy is:

1 Gordy=1 mm$^{-1}$.

The laminate of paper/polymer/paper used in the present invention preferably comprises the ethylene/vinyl acetate copolymer and/or the ionomer resin in a thickness, measured as a coating rate, in the range of from 5 to 30 g/mm$^2$, more preferably 10 to 20 g/mm$^2$.

It will be understood that the polymer layer in the laminate may comprise the ethylene/vinyl acetate copolymer alone, an ionomer resin alone or a combination of layers of these polymers. The polymer swells when in contact with the fragrance components and the swellability of the polymer affects the rate of passage of the fragrance component through the laminate.

The laminate may be prepared by any suitable method. For example, a sheet of paper may be coated with the polymer in the desired thickness range and a second sheet of paper laminated thereto, for example by passing the laminate through heated rollers, or any other suitable means. Alternatively, two separate sheets of paper may be coated with the polymer and then laminated together, i.e. two single sheets of paper may each be coated with a weight 5 g/m$^2$ of the polymer and then laminated together to form a polymer layer 10 g/m² thick. An advantage of coating onto each of the sheets of paper, rather than just onto one, is that the presence of pin holes through the polymer layer is avoided. If desired or necessary, an adhesive may also be used to laminate two polymer coated paper sheets together. However, any adhesive used must be resistant to the swelling action of the volatile liquid. The polymer coating on the paper sheet is generally applied as an aqueous dispersion in water.

The paper which is used to form the laminate preferably has a weight in the range of from 25 to 100 g/m² more preferably from 30 to 50 g/m², yet more preferably a weight of about 40 g/m².

The paper which is used to form the laminate is preferably a machine glazed paper which is specifically designed for coating with aqueous coatings. The coatings are generally applied to the glazed surface and thus when the laminate is formed the glazed surfaces are in the middle of the sandwich. The rougher sides of the paper are then available for sealing to the dispenser, for example by the use of heat and/or pressure. The paper/polymer/laminate is preferably sealed with a removable, vapour impermeable barrier, such as an aluminium foil, for storage purposes.

For example, if the dispenser is made from a thermoplastics material then the method and apparatus as disclosed in WO-A-93/10959 may be used to seal the laminate to the dispenser.

The ethylene/vinyl acetate copolymer used in the present invention preferably has a vinyl acetate content in the range of from 15 to 33% by weight of vinyl acetate, more preferably 20 to 30% by weight of vinyl acetate.

The melt index of the ethylene/vinyl acetate copolymer should preferably be in the range of from 1 to 500 g/min, more preferably in the range of from 6 to 200 g/min.

Suitable ethylene/vinyl acetate copolymer dispersions for use in the present invention are those sold under the Trademark Adcote obtainable from Morton International.

The ionomer resin which is used in the present invention is preferably an ethylene/methacrylic acid copolymer as the sodium or zinc ionomer which is sold under the Trademark Surlyn.

The device of the present invention is preferably used for the controlled release of air freshener liquids, for example perfumes; insecticidal liquids; insect repellent; deodorants; or odorising jewellery or personal decorations.

The volatile liquid used in the devices of the present invention preferably has a dipole moment in the range of from 1 to 2 Debyes and preferably also has a hydrogen bonding parameter of from 5 to 15 Gordys. The device is particularly useful for dispensing fragrances which cannot effectively be used with the device as described in EP-A-0260896. Examples of such fragrance components include cedar wood oil, alpha ionone, dihydro myrcenol, lavandin oil grosso, benzyl acetate and geranyl acetate. These fragrance components may be used alone, in admixture with one another, or in admixture with one or more other fragrance components.

The volatile liquid which is contained in the devices of the present invention may contain a proportion of less volatile or relatively non-volatile materials which do not totally evaporate in a given time. Preferably, for a composition intended to be volatilised in about 30 days, it should contain no more than about 10% w/w of such non-volatiles. More particularly, such a composition should preferably contain no more than 7.5% w/w of non-volatiles.

The rate of emanation is important in determining the life of the devices in accordance with the present invention and this is controlled by the emanator surface area, the chemical and physical properties of the volatile liquid, as well as the nature of the polymer in the laminate and its thickness.

Although the thickness of an ethylene/vinyl acetate copolymer does not significantly affect the rate of emanation through the laminate, the situation is different for an ionomer resin such as Surlyn where a thicker polymeric layer will decrease the rate of emanation.

For use as an air freshener, the desired rate of emanation from the laminate is of the order of 6 grams over a period of 30 days.

A simple test, the so called "Swelling Test", is indicative of the utility in the present invention of a particular laminate-liquid combination. The "Swelling Test" involves the drying of ethylene/vinyl acetate copolymer emulsions and ionomer resin (Surlyn) emulsions to form viscous melts which were then cast into thin slabs approximately 2 mm thick. Rectangular pieces of these slabs are suspended in a fragrance and the changes in weight and volume expressed as a percentage of the original weight and volume.

For laminates based on ethylene/vinyl acetate copolymer an increase in weight of above 10% within four days is regarded as a useful laminate for the fragrance of choice, whereas for Surlyn an increase in weight of above 4% within four days is regarded as a useful laminate for the fragrance of choice.

BRIEF DESCRIPTION OF THE DRAWINGS

The present invention will be further described with reference to FIGS. 1 and 2 of the accompanying drawings in which.

Figure 1:
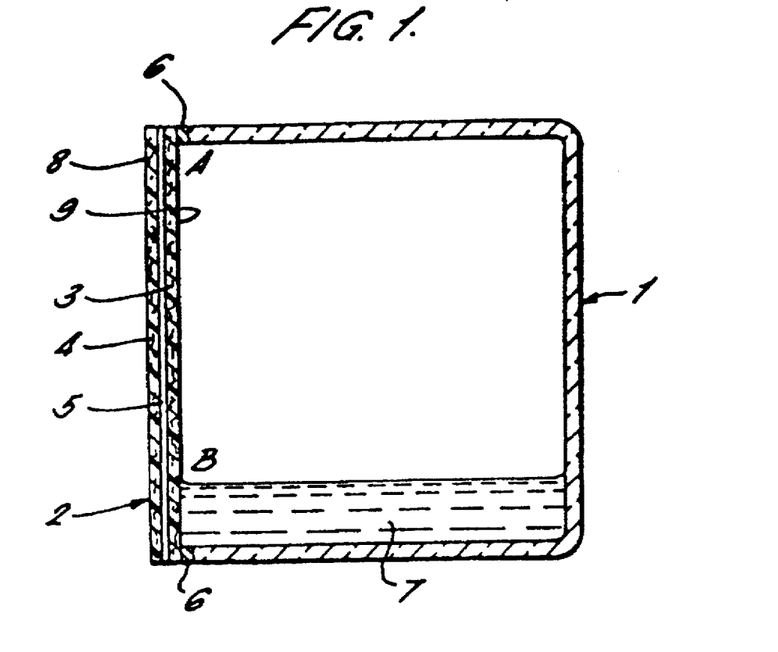
FIG. 1 is a vertical section through an emanator device in accordance with the present invention in one operating position.
Figure 2:
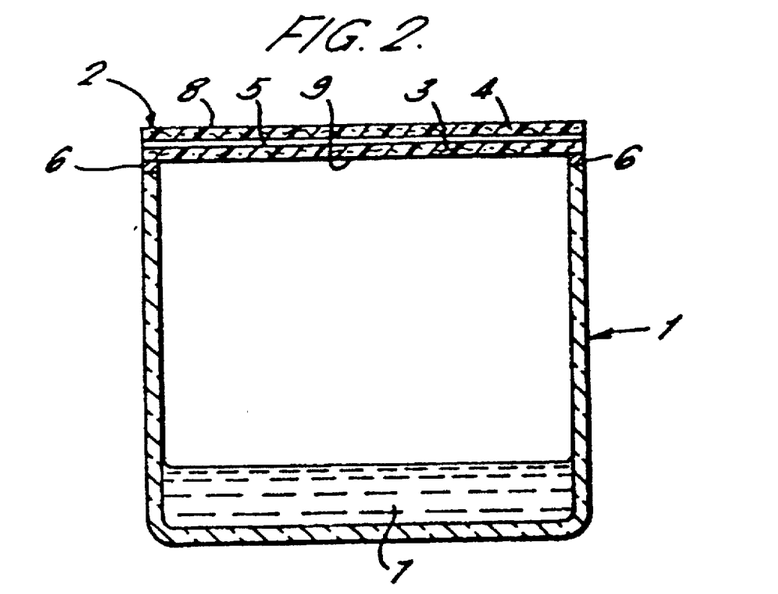
FIG. 2 illustrates the device of FIG. 1 rotated through a right angle in another operating position.
Figure 3:
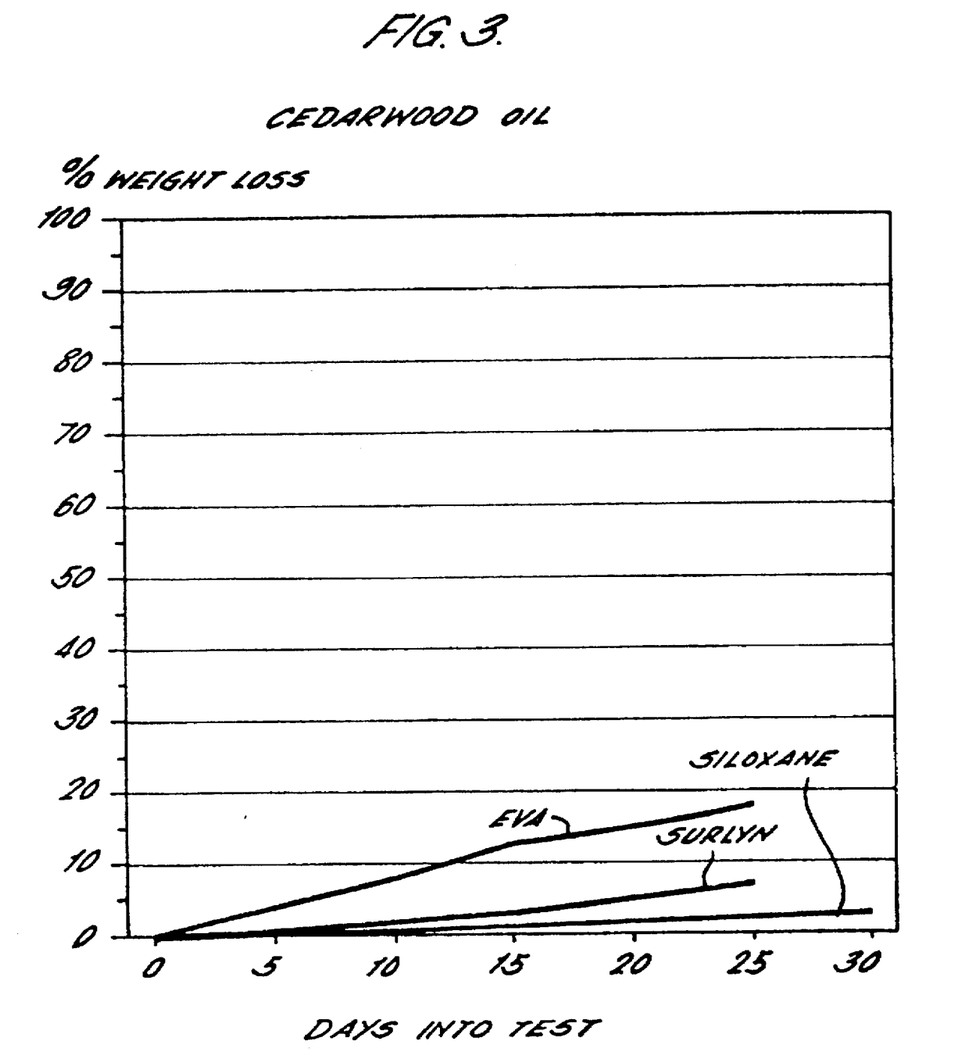
FIGS. 3, 4, 5, and 6 are graphs showing data obtained in Example 1.
Figure 4:
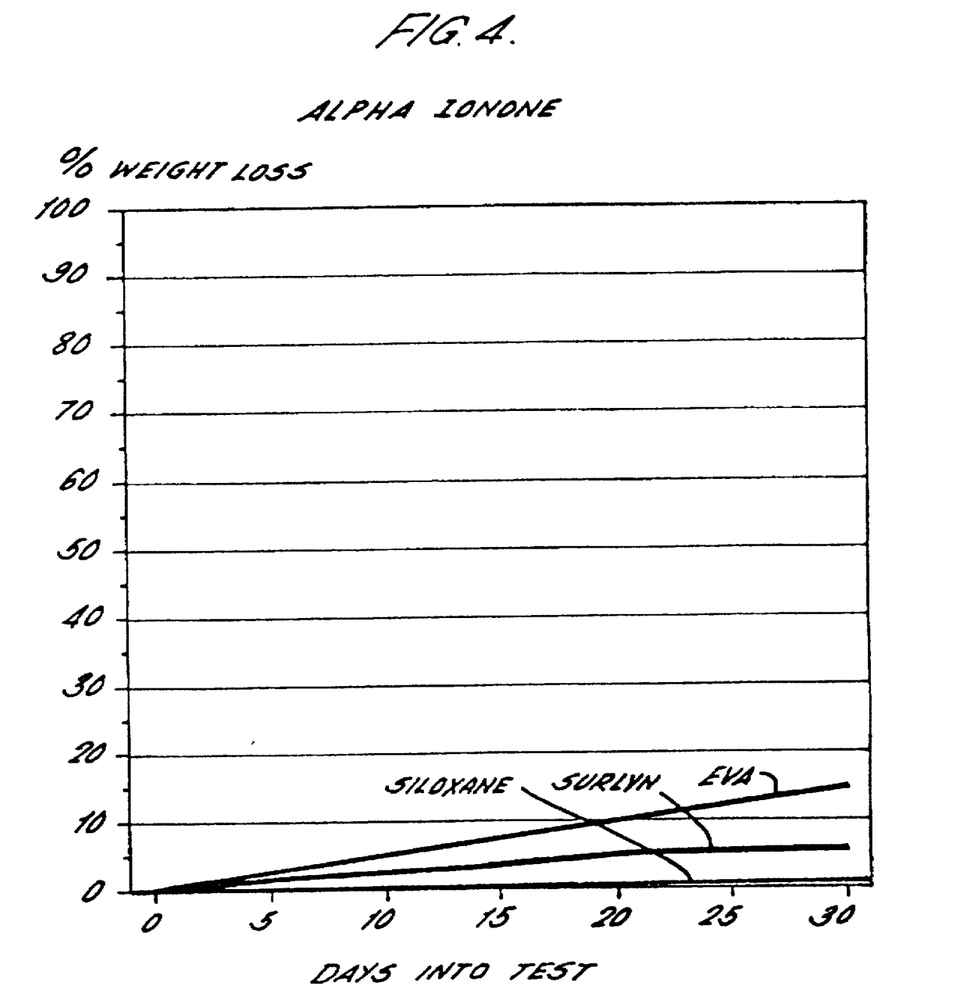
Figure 5:
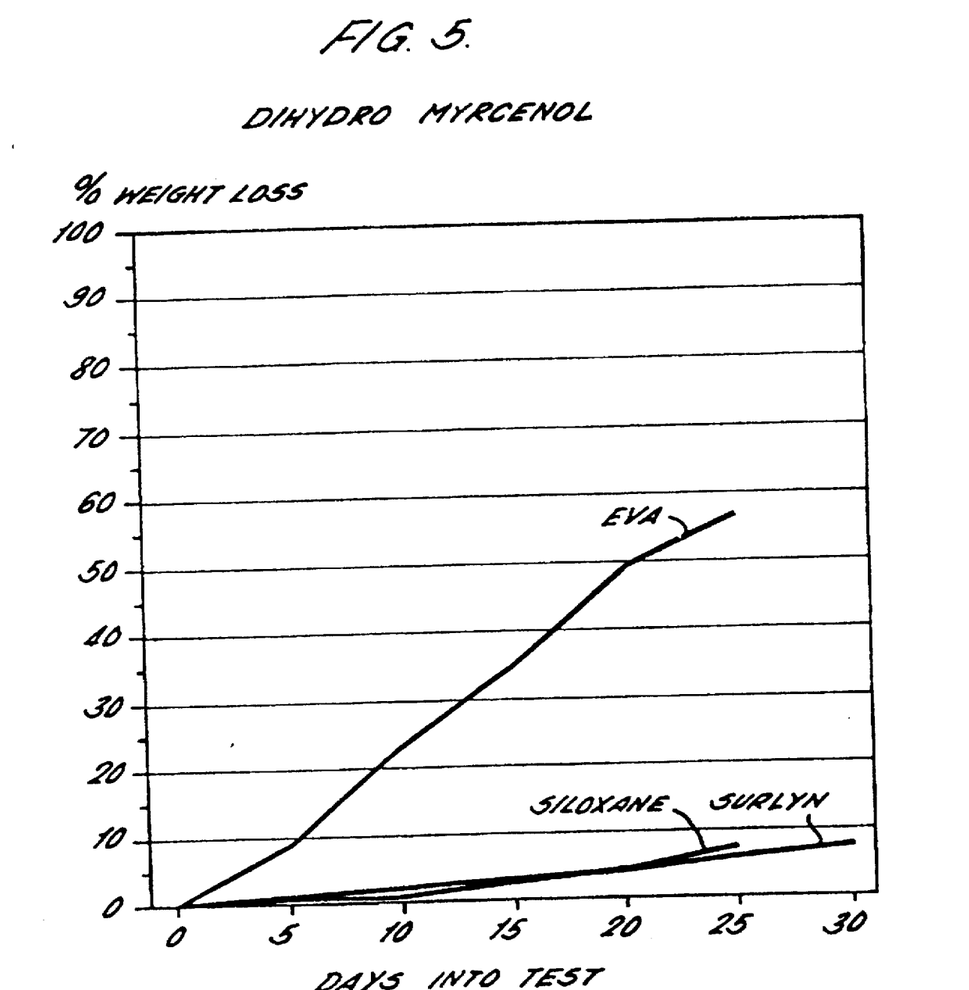
Figure 6:
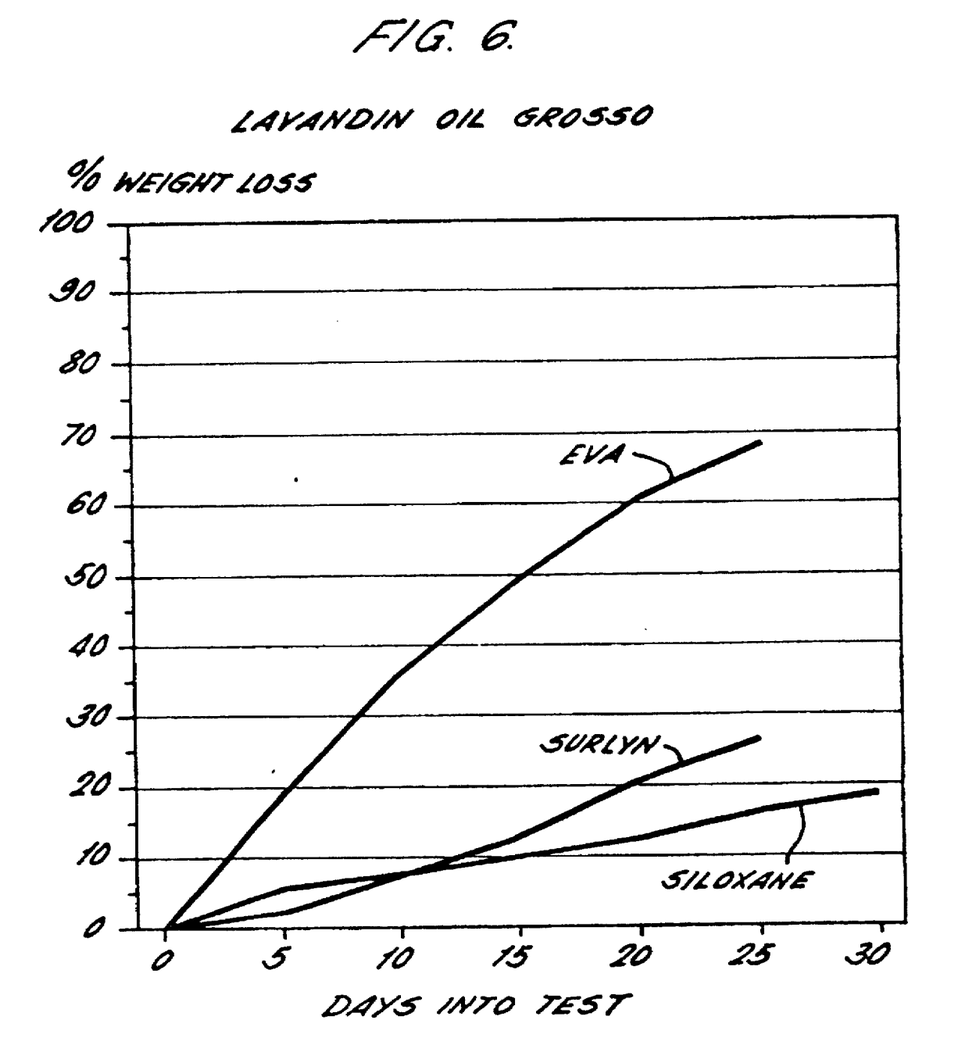

Referring to the drawings, an open topped glass container 1 is closed by a porous laminate generally shown at 2. The laminate comprises two sheets of paper 3 and 4 which are laminated together with one or a plurality of layers of ethylene/vinyl acetate (EVA) shown at 5.

The laminate 2 is sealed around its periphery across the container opening with a sealant to provide a liquid proof seal 6.

A volatile liquid 7 is contained in the container 1. As shown in FIG. 1, the liquid 7 is in contact with the impregnated laminate 2; in FIG. 2, the liquid 7 does not contact the impregnated laminate unless and until the device is tipped on its side or inverted.

For storage, the exterior side 8 of the laminate 2 is protected by a removable sheet of an impermeable material, such as aluminium foil (not shown), to prevent wasteful loss of vapour during storage.

Referring now to the device in the operating position as shown in FIG. 1, the volatile liquid 7 contacts only an edge of the laminate 2 below B on the inner face 9. The laminate 2 absorbs liquid 7 so that it is constantly impregnated therewith during operation and the free space above the liquid 7 in the container 1 is constantly saturated with vapour of the 1 liquid 7.

Transmission through the impregnated laminate occurs and the vapour emanates from the outer surface 8 thereof in a substantially linear fashion over a period of time. This is a consequence of the dynamic equilibrium which exists whilst some liquid 7 remains in the container 1. No wetting of outer surface 8 is detectable and no liquid 7 is lost from the container as liquid providing that the seal 6 is adequate. A continuous emanation is thus achieved.

When the liquid 7 is exhausted, the fact is apparent on visual inspection provided the container is constructed of a translucent material.

In an alternative operating position depicted in FIG. 2 the porous laminate is wetted with volatile liquid 7 by inverting the container 1. In this way an intermittent emanation can be produced as and when desired by reinverting the container 1 whereupon emanation ceases or is significantly reduced when the volatile liquid absorbed by the porous element is temporarily exhausted.

The device can therefore be used as a constant emission device or as an intermittent emission device, thus giving a measure of control over rates of emission.

Devices in accordance with the invention have the advantages of:

(i) an end-of-life indicator is available in that the reservoir of treatment material may be translucent so that a user can observe the level of contained liquid by visual inspection;
(ii) where there is no need for a removable-replaceable closure they can be leakproof;
(iii) complete discharge of contents is assured;
(iv) in some cases relatively constant release with respect to temperature variation is achieved; and
(v) since wrapping at manufacture need be only a tear-off impermeable strip over the mechanical support, they are easily accessible; moreover beneath the tear-off strip the outer surface is charged with vapour immediately it is uncovered, that is the substance is readily accessible.

The present invention will be further described with reference to the following examples which illustrate slow release perfume containers falling within the scope of the present invention.

EXAMPLE 1

A machine glazed bleached kraft paper having a basis weight of 40 g/m$^2$ was coated with 5 g/m$^2$ of Surlyn (grade 56220 Poly Chimie) from an emulsion.

The coated paper was then laminated to a similar coated paper by passing the web through hot nip rollers operating at a temperature of 120° C. to form a laminate of paper/10 g/m$^2$ Surlyn/paper.

Portions of the laminate were sealed to the mouths of small glass containers in which were placed quantities of perfumes selected from Chinese cedarwood oil, alpha ionone 700 (Bush Boake Allen), dihydro myrcenol (perfumery quality) and lavendin oil grosso.

The devices were moved to a specially set-up emanation room, having a temperature of 21° C. ±2° C., a relative humidity of 55%±3% and an average air flow of 0.1 m/s.

The devices were placed in an inverted position so that the perfume was in contact with the laminate and the untreated side of the laminate was substantially open to the ambient air. After a relatively short period of time it was evident that the particular perfume was emanating into the surrounding air.

The percentage weight loss of the perfumes from the devices was also recorded and the results are shown in FIGS. 3, 4, 5 and 6.

FIGS. 3, 4, 5 and 6 also provide details of perfume weight losses for cedarwood oil, alpha ionone, dihydro myrcenol and lavendin oil grosso with a laminate of paper/15 g/m$^2$ EVA/paper prepared as described above, the EVA being grade 37R972 from Morton International, and a siloxane coated (1 g/m$^2$) paper laminate according to EP-A-0260896.

EXAMPLE 2

Figure 7:
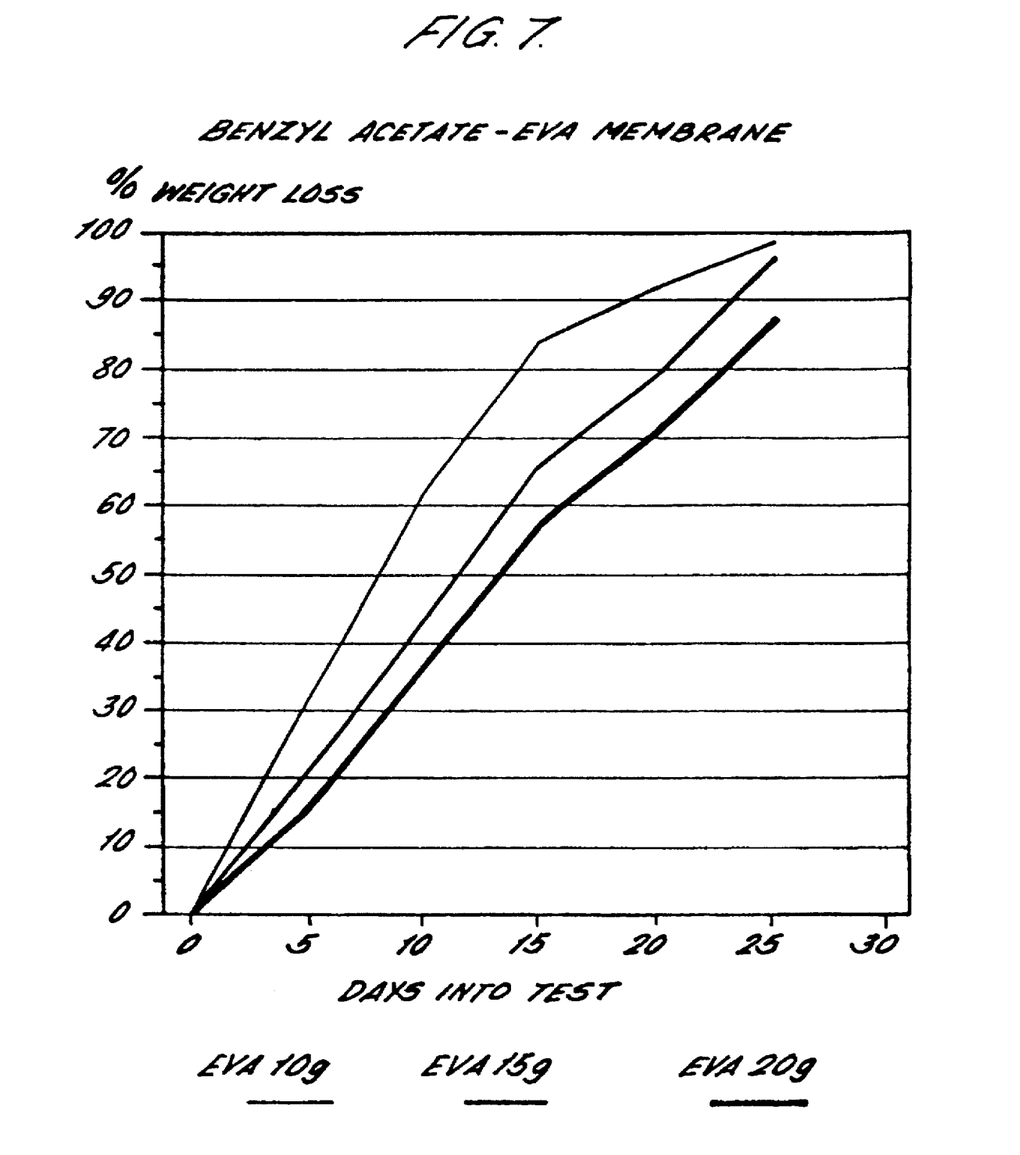
FIGS. 7 and 8 are graphs showing data reported in Example 2.
Figure 8:
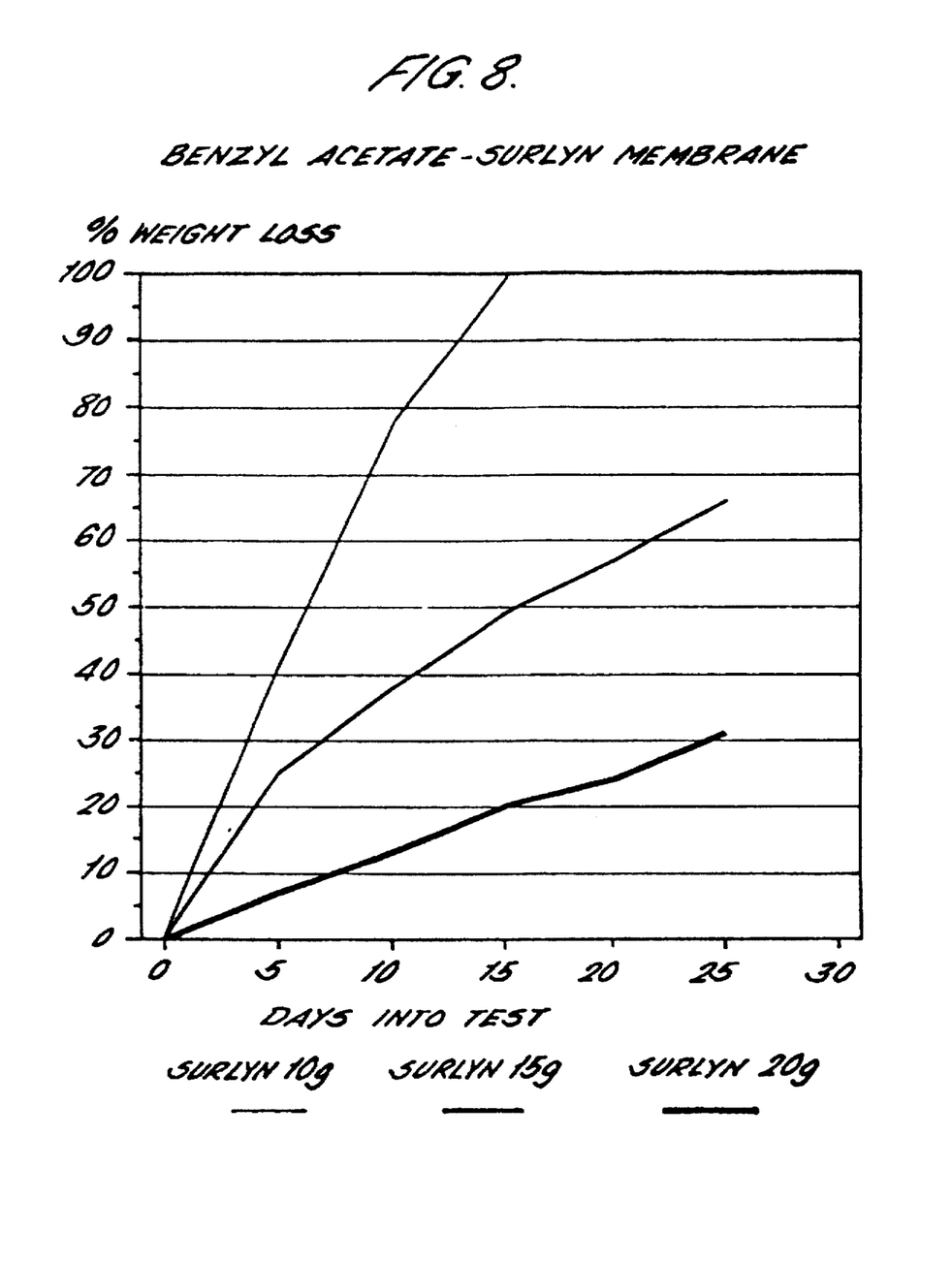

The passage of the commonly used fragrance component benzyl acetate (perfumery quality) through various thicknesses (expressed as coating weights per square meter) of EVA and Surlyn are shown in FIGS. 7 and 8.

In each case the paper/EVA/paper laminate or the paper/Surlyn/paper laminate was prepared according to the method as described in Example 1.

It can be seen from these Figures that the EVA emanates at approximately the same rate irrespective of thickness, whilst the emanation of the fragrance component through the Surlyn containing laminate is considerably reduced by increasing the coating weight.

EXAMPLE 3

Figure 9:
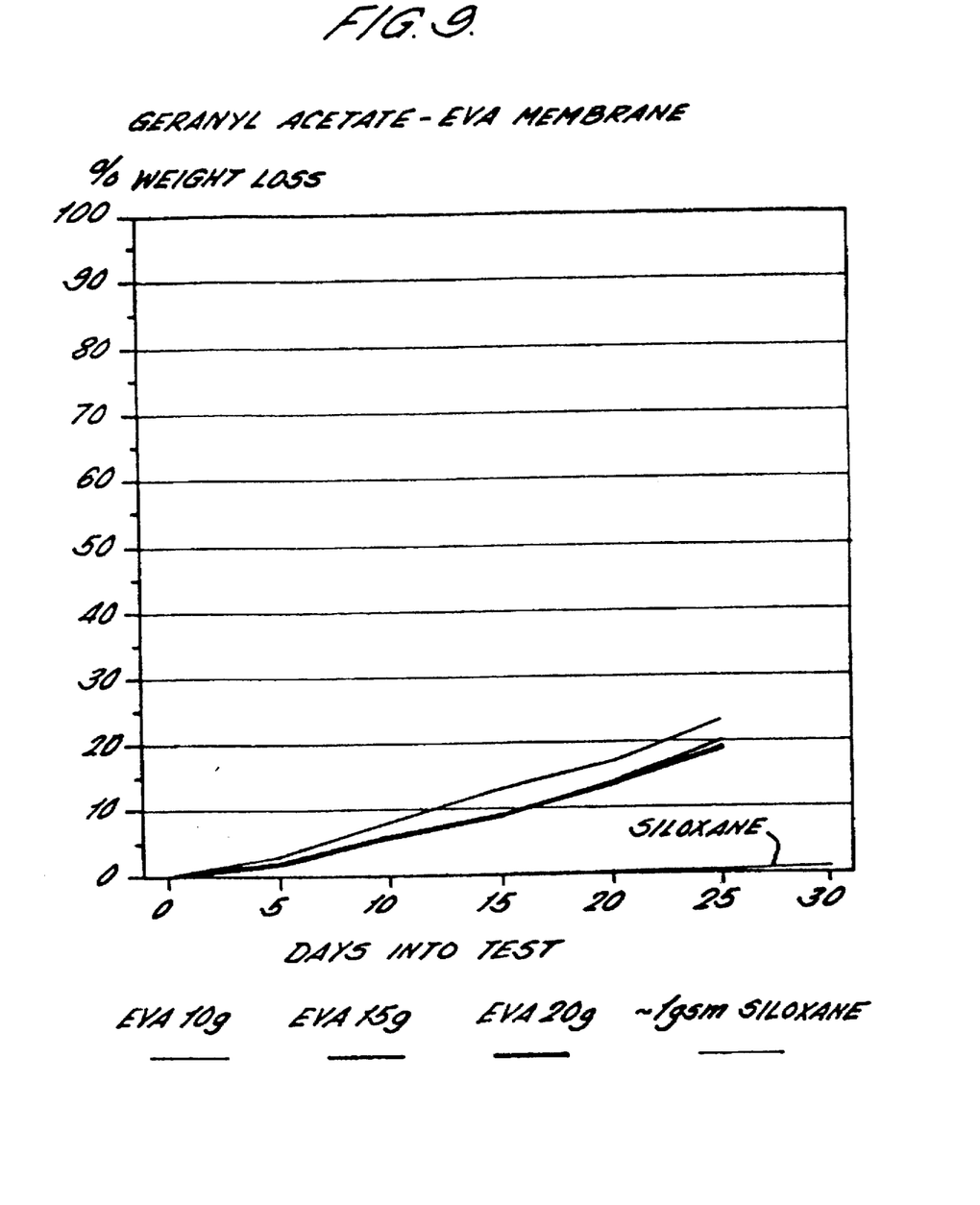
FIGS. 9 and 10 are graphs showing data reported in Example 3.
Figure 10:
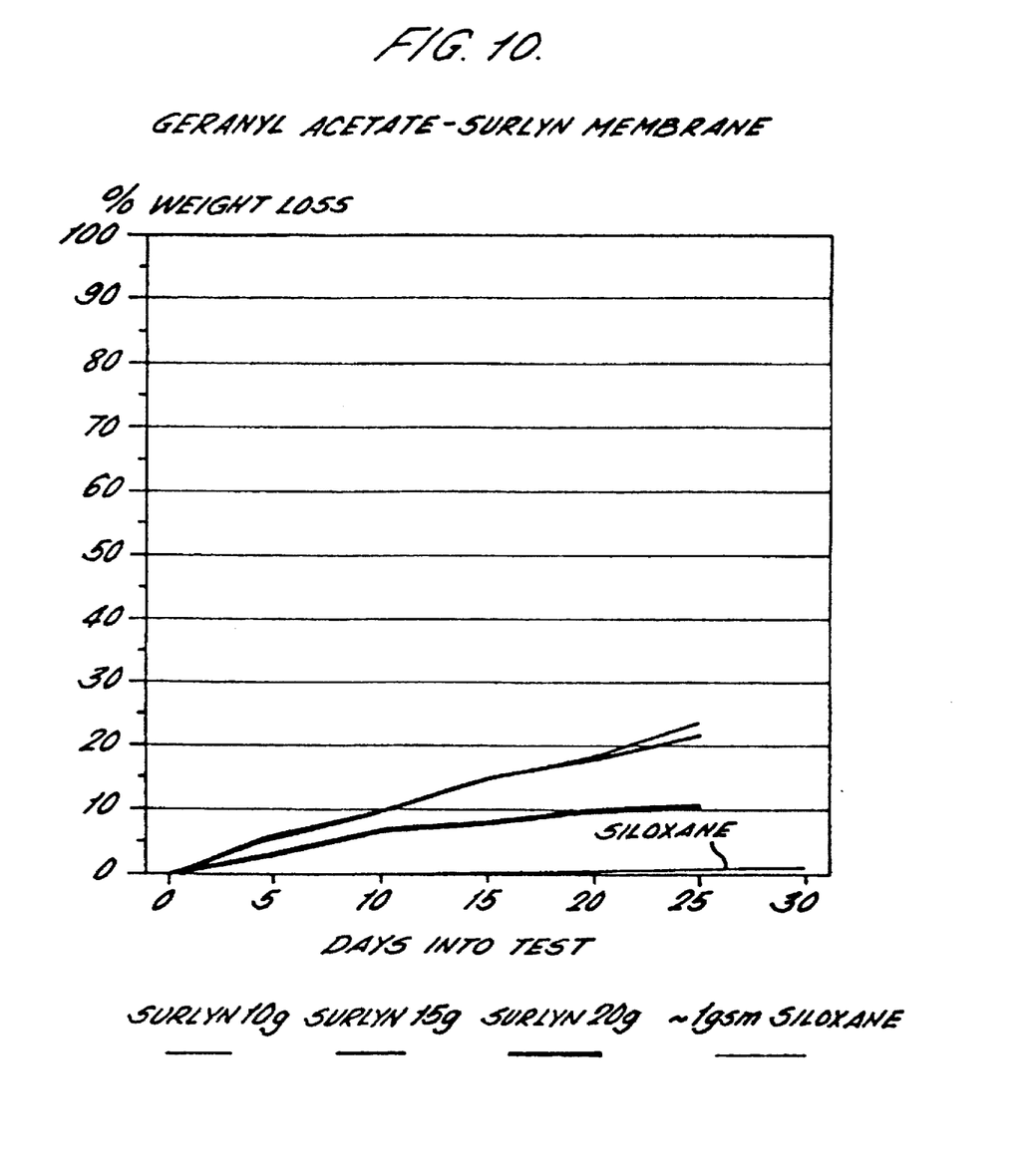

The passage of the commonly used fragrance component geranyl acetate (Bush Boake Allen) through various thicknesses (expressed as coating weights per square meter) of EVA and Surlyn are shown in FIGS. 9 and 10.

In each case the paper/EVA/paper laminate or the paper/Surlyn/paper laminate was prepared according to the method as described in Example 1.

It can be seen from these Figures that the EVA emanates at approximately the same rate irrespective of thickness, whilst the emanation of the fragrance component through the Surlyn containing laminate is considerably reduced by increasing the coating weight. The graphs also show the rate of emanation for a siloxane coated (1 g/m$^2$) paper laminate according to EP-A-0260896.

I claim:

1. A device for dispensing a volatile liquid as a vapour comprising a reservoir for the volatile liquid, a volatile liquid and a porous element which permits the passage of vapour therethrough but does not permit the passage of said liquid therethrough, said porous element comprising a laminate of paper/polymer/paper, said polymer selected from the group consisting of a copolymer of ethylene and vinyl acetate and a sodium or zinc ionomer of a copolymer of ethylene and methacrylic acid, and said volatile liquid comprising one or more fragrance components having a dipole moment in the range of from 0 to 3 Debyes and a hydrogen bonding parameter of from 0 to 22 Gordys.

2. The device of claim 1 wherein said polymer has a thickness, measured as a coating weight, in the range of from 10 to 20 g/m$^2$.

3. The device of claim 1 wherein said laminate is sealed with a removable, vapour impermeable barrier for storage purposes.

4. The device of claim 1 wherein said volatile liquid has a dipole moment in the range of from 1 to 2 Debyes.

5. The device of claim 1 wherein said volatile liquid has a hydrogen bonding parameter of from 5 to 15 Gordys.

6. The device of claim 1 wherein said paper/polymer/paper laminate is heat sealed to a container containing the reservoir of the volatile liquid.

7. The device of claim 1 wherein each paper sheet in the laminate has a weight in the range of from 30 to 50 g/m$^2$.

8. The device of claim 1 wherein said porous element comprises two laminates of paper/polymer which are laminated together with the polymer layers in face-to-face contact in the interior of said laminate.

9. The device of claim 8 wherein an adhesive is used to laminate the two polymers layers together, said adhesive being selected so as to be resistant to the swelling action of said volatile liquid.

* * * * *